(12) United States Patent
Schleich et al.

(10) Patent No.: US 9,750,937 B2
(45) Date of Patent: Sep. 5, 2017

(54) RATE AND PLACE OF STIMULATION MATCHED TO INSTANTANEOUS FREQUENCY

(71) Applicant: MED-EL Elektromedizinische Geraete GmbH, Innsbruck (AT)

(72) Inventors: Peter Schleich, Telfs (AT); Reinhold Schatzer, Birgitz (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 15/079,131

(22) Filed: Mar. 24, 2016

(65) Prior Publication Data

US 2016/0279414 A1    Sep. 29, 2016

Related U.S. Application Data

(60) Provisional application No. 62/212,642, filed on Sep. 1, 2015, provisional application No. 62/212,643, filed on Sep. 1, 2015.

(30) Foreign Application Priority Data

Mar. 26, 2015 (DE) .................. 10 2015 104 614

(51) Int. Cl.
*A61N 1/36* (2006.01)
*A61N 1/05* (2006.01)
*H04R 25/00* (2006.01)

(52) U.S. Cl.
CPC ....... *A61N 1/36032* (2013.01); *A61N 1/0541* (2013.01); *H04R 25/48* (2013.01); *H04R 25/502* (2013.01); *H04R 25/70* (2013.01)

(58) Field of Classification Search
None
See application file for complete search history.

(56) References Cited

U.S. PATENT DOCUMENTS 5,800,475 A * 9/1998 Jules .................. A61N 1/36032
                                                                      607/57
7,979,135 B2    7/2011 Arnoldner et al.
(Continued)

FOREIGN PATENT DOCUMENTS

DE    102015104614    3/2015
WO    WO 96/34508    10/1996
WO    WO 01/19135    3/2001

OTHER PUBLICATIONS

International Searching Authority, German International Search Report for PCT/EP2016/056636, dated Jun. 22, 2016, 8 pages.
(Continued)

*Primary Examiner* — Brian T Gedeon
(74) *Attorney, Agent, or Firm* — Sunstein Kann Murphy & Timbers LLP

(57) ABSTRACT

A signal processing arrangement generates electrical stimulation signals to stimulation contacts in an implanted cochlear implant array. An input sound signal is decomposed into dominant psychophysically relevant frequency components, with each frequency component changing over time in frequency and level. Each frequency component is coded as a patient-specific, frequency-specific function of stimulation location, rate, and level to produce a sequence of requested stimulation events having an instantaneous frequency and level. And the electrical stimulation signals are generated from the requested stimulation events for delivery by the stimulation contacts to adjacent auditory neural tissue.

21 Claims, 12 Drawing Sheets

(5 of 12 Drawing Sheet(s) Filed in Color)

(56) References Cited

U.S. PATENT DOCUMENTS

| | | |
|---|---|---|
| 8,532,782 B2 | 9/2013 | Bräcker et al. |
| 8,554,330 B2 | 10/2013 | Bradley et al. |
| 2005/0203589 A1 | 9/2005 | Zierhofer |
| 2006/0235486 A1 | 10/2006 | Blamey et al. |
| 2007/0179565 A1 | 8/2007 | Overstreet et al. |
| 2009/0012580 A1 | 1/2009 | Arnoldner et al. |
| 2010/0185261 A1 | 7/2010 | Schleich |
| 2010/0249879 A1 | 9/2010 | Bräcker et al. |
| 2010/0292754 A1 | 11/2010 | Gliner |
| 2011/0066210 A1 | 3/2011 | Wilson |
| 2011/0077712 A1 | 3/2011 | Killian |
| 2011/0230934 A1 | 9/2011 | Zierhofer |
| 2012/0004706 A1 | 1/2012 | Meister et al. |
| 2014/0005746 A1 | 1/2014 | Schleich et al. |
| 2015/0088225 A1 | 3/2015 | Noble et al. |
| 2015/0163605 A1 | 6/2015 | Meister et al. |

OTHER PUBLICATIONS

Verbist, et al, "Consensus Panel on a Cochlear Coordinate System Applicable in Histologic, Physiologic and Radiologic Studies of Human Cochlea", *Otology & Neurotogy*, 31:722-370, 2010, 10 pages.

Kestner, "Cochlear-Implanta-Systeme", Schauenburg: Karin Kester Verlag, 2005. 9-1-1-9-910, http://www.kestner.de/n/verschiedenes/presse/2005/ImplKat_Cochlea-2005.pdf, 55 pages.

Bonham et al., "Current focusing and steering: Modeling, physiology, and psychophysics," NIH Public Access Author Manuscript, vol. 242, No. 1-2, 27 pages, Aug. 2008.

Hochmair, et al., "MED-EL Cochlear Implants: State of the Art and a Glimpse Into the Future," Trends in Amplification, vol. 10, No. 4, pp. 201-220, Dec. 2006.

Loeb, "Are Cochlear Implant Patients Suffering From Perceptual Dissonance?," Ear & Hearing, pp. 435-450, Oct. 2005.

Secker-Walker et al., "Time-domain analysis of auditory-nerve-fiber firing rates," Journal of Acoustical Society of America, vol. 88, No. 3, pp. 1427-1436, Sep. 1990.

International Searching Authority, International Search Report—International Application No. PCT/US16/41041, dated Sep. 7, 2016, together with the Written Opinion of the International Searching Authority, 10 pages.

International Searching Authority, International Search Report—International Application No. PCT/US16/41042, dated Sep. 16, 2016, together with the Written Opinion of the International Searching Authority, 13 pages.

* cited by examiner

RATE AND PLACE OF STIMULATION MATCHED TO INSTANTANEOUS FREQUENCY This application claims priority from German Patent Application DE 102015104614, filed Mar. 26, 2015, from U.S. Provisional Patent Application 62/212,643, filed Sep. 1, 2015, and from U.S. Provisional Patent Application 62/212,642, filed Sep. 1, 2015, all of which are incorporated herein by reference in their entireties.

FIELD OF THE INVENTION

The present invention relates to hearing implant systems, and more specifically, to techniques for producing electrical stimulation signals in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple stimulation contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple stimulation contacts 112 on its surface that provide selective stimulation of the cochlea 104. Depending on context, the stimulation contacts 112 are also referred to as electrode channels. In cochlear implants today, a relatively small number of electrode channels are each associated with relatively broad frequency bands, with each stimulation contact 112 addressing a group of neurons with an electric stimulation pulse having a charge that is derived from the instantaneous amplitude of the signal envelope within that frequency band.

In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

FIG. 2 shows the major functional blocks in a typical cochlear implant signal processing system wherein band pass signals are processed and coding to generate electrode stimulation signals to stimulation electrodes in an implanted cochlear implant electrode array. For example, commercially available Digital Signal Processors (DSP) can be used to perform speech processing according to a 12-channel CIS approach. The initial acoustic audio signal input is produced by one or more sensing microphones, which may be omnidirectional and/or directional. Preprocessor Filter Bank 201 pre-processes the initial acoustic audio signal with a bank of multiple band pass filters, each of which is associated with a specific band of audio frequencies—for example, a digital filter bank having 12 digital Butterworth band pass filters of 6th order, Infinite Impulse Response (IIR) type—so that the acoustic audio signal is filtered into some M band pass signals, $B_1$ to $B_M$, where each signal corresponds to the band of frequencies for one of the band pass filters. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each stimulation contact in the scala tympani often is associated with a specific band pass filter of the external filter bank.

FIG. 3 shows an example of a short time period of an audio speech signal from a microphone, and FIG. 4 shows an acoustic microphone signal decomposed by band-pass filtering by a bank of filters into a set of signals. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels − 1 do
    for s = 0 to number of samples − 1 do
        Y_j(s) = B_{0j} * X_j(s) + Z_{0j}
        for i = 0 to order − 3 do
            Z_{i,j} = B_{i+1,j} * X_j(s) + Z_{i+1,j} − A_{i+1,j} * Y_j(s)
        end for
        Z_{order − 2,j} = B_{order − 1,j} * X_j(s) − A_{order − 1,j} * Y_j(s)
    end for
end for
```

The band pass signals $B_1$ to $B_M$ (which can also be thought of as frequency channels) are input to a Signal Processor 202 which extracts signal specific stimulation information—e.g., envelope information, phase information, timing of requested stimulation events, etc.—into a set of N stimulation channel signals $S_1$ to $S_N$ that represent electrode specific requested stimulation events. For example, channel specific sampling sequences (CSSS) may be used as described in U.S. Pat. No. 6,594,525, which is incorporated herein by reference in its entirety. For example, the envelope extraction may be performed using 12 rectifiers and 12 digital Butterworth low pass filters of 2nd order, IIR-type.

A Pulse Generator 205 includes a Pulse Mapping Module 203 that applies a nonlinear mapping function (typically logarithmic) to the amplitude of each band-pass envelope. This mapping function—for example, using instantaneous nonlinear compression of the envelope signal (map law)—typically is adapted to the needs of the individual cochlear implant user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_M$ that provide an optimal electric representation of the acoustic signal. A logarithmic function with a form-factor C typically may be applied as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals $A_1$ to $A_M$ outputs from the Pulse Mapping Module 203.

The Pulse Generator 205 also includes a Pulse Shaper 204 that develops the set of electrode stimulation signals $A_1$ to $A_M$ into a set of output electrode pulses $E_1$ to $E_M$ for the electrode contacts in the implanted electrode array which stimulate the adjacent nerve tissue. The electrode stimulation signals $A_1$ to $A_M$ may be symmetrical biphasic current pulses with amplitudes that are directly obtained from the compressed envelope signals.

In the specific case of a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

Another cochlear implant stimulation strategy that does transmit fine time structure information is the Fine Structure Processing (FSP) strategy by Med-El. Zero crossings of the band pass filtered time signals are tracked, and at each negative to positive zero crossing, a Channel Specific Sampling Sequence (CSSS) is started. Typically CSSS sequences are only applied on the first one or two most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

Many cochlear implant coding strategies use what is referred to as an N-of-M approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

One method to reduce the spectral clustering of stimulation per time frame is the MP3000™ coding strategy by Cochlear Ltd, which uses a spectral masking model on the electrode channels. Another method that inherently enhances coding of speech onsets is the ClearVoice™ coding strategy used by Advanced Bionics Corp, which selects electrode channels having a high signal to noise ratio. U.S. Patent Publication 2005/0203589 (which is incorporated herein by reference in its entirety) describes how to organize electrode channels into two or more groups per time frame. The decision which electrode channels to select is based on the amplitude of the signal envelopes.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc. But some stimulation arrangements are quite power consuming, especially when neighboring electrodes are used as current sinks. Up to 10 dB more charge might be required than with simple mono-polar stimulation concepts (if the power-consuming pulse shapes or stimulation modes are used continuously).

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been investigated (e.g. by Vermeire et al., *Neural tonotopy in cochlear implants: An evaluation in* unilateral cochlear implant patients with unilateral deafness and tinnitus, Hear Res, 245(1-2), 2008 Sep. 12 p. 98-106; Schatzer et al., *Electric-acoustic pitch comparisons in single-sided-deaf cochlear implant users: Frequency-place functions and rate pitch*, Hear Res, 309, 2014 March, p. 26-35; both of which are incorporated herein by reference in their entireties). High rate single electrode stimuli have been matched to acoustic stimuli received through a normal hearing contralateral ear. FIG. 5 shows an example of prototype frequency percept in response to high rate stimulation (1500 pps) over distance along the basilar membrane from the round window.

It is also known in the field that different stimulation rates produce different pitch percepts at different apical electrodes (Schatzer et al., 2014; Prentiss et al., *Ipsilateral acoustic electric pitch matching: a case study of cochlear implantation in an up-sloping hearing loss with preserved hearing across multiple frequencies*, Cochlear Implants Int., 15(3), 2014 May, p. 161-165; incorporated herein by reference in its entirety). More apical electrodes produce even lower pitch percepts at lower stimulation rates. On the other hand, rate-pitch saturation limits (i.e. the rate above which no more useful change in pitch occurs) have been identified to be as high as 900 Hz (Kong et al., *Temporal pitch perception at high rates in cochlear implants*, J. Acoust. Soc. Am., 127(5), 2010 May, p. 3114-3123; incorporated herein by reference in its entirety). On individual electrodes, preferably in the apical region of the cochlea, the frequency range that is perceivable by varying the stimulation rate can be relatively large.

FIG. 6 shows examples of the frequency percepts elicited at different intracochlear stimulation locations by different stimulation rates. On an apical electrode, a stimulation rate of 100 pps might sound like an acoustic sound with a fundamental frequency (F0) of 80 Hz, whereas a stimulation rate of 1500 pps might sound like an acoustic stimulus with an F0 of 900 Hz. However, the perceived frequency for a given stimulation location and rate can also change as a function of stimulation level (or current in µA; Vandali et al., *Pitch and loudness matching of unmodulated and modulated stimuli in cochlear implantees*, Hear Res., 302, 2013 August, p. 32-49, incorporated herein by reference in its entirety).

In a typical cochlear implant system, the most apical electrode is assigned to a relatively narrow band pass filter, e.g. 100-200 Hz. In coding strategies such as FSP, which are designed to code temporal fine structure information, typical stimulation rates of 100 to 200 pps are derived for the specific electrode. Such systems are known to have various limitations including:

A possible change of perceived frequency as a function of stimulation current level for a given stimulation location and rate is not taken into account (see FIG. 7 which shows frequency percepts elicited at different intracochlear stimulation locations by different stimulation rates delivered at different stimulation current levels).

The available range of perceived frequencies coded by different stimulation rates is restricted to the band pass limits of the assigned filters (see FIG. 8 which shows non-overlapping frequency ranges perceived by stimulating three adjacent electrode locations at band-specific stimulation rates).

A change in instantaneous frequency of an input frequency component is only partly translated into a change of stimulation location (Instantaneous stimulation rates within the analyzed frequency range stay at the location of the electrode, see FIG. 8).

Multiple frequency components within one band pass filter cannot be assigned a specific stimulation location and rate.

Band pass filters define the frequency range transmitted by a given physical electrode, or by a virtual electrode that stimulates two adjacent electrodes either simultaneously or in rapid succession. Temporal fine structure coding strategies apply rate code to an electrode assigned to a given filter band. Adjacent electrodes or electrode combinations are typically assigned to adjacent filter bands. Individual frequency components can be assigned to pre-defined, amplitude-weighted simultaneously-stimulated electrodes, as in U.S. Patent Publication 2010/0185261 (which is incorporated herein by reference in its entirety). This type of signal analysis limits electrode pitches to the assigned frequency range and disregards lower and higher pitches produced by rates that are lower or higher, respectively, than the band frequency limits. In addition, continuous changes in input frequency are only represented as continuous changes in stimulation rate or rate of pulse packages, but not as continuous shifts in simulation location. And also, the influence on perceived frequency of stimulation level for a given stimulation location and rate is not taken into account.

U.S. Pat. No. 8,554,330 describes a different method of electrode location-pitch matching by indirectly measuring an individual cochlear location-frequency map based on acoustic auditory brainstem response (ABR). This individual location-frequency map is used to either position an electrode within the cochlea so as to match the electrode location to the individual location-frequency map, or to map an already inserted electrode so as to provide "stimuli only to the parts of the cochlea that have reduced or no residual hearing." This approach requires that residual hearing be sufficiently preserved to measure the individual location-frequency map via acoustic ABR, and therefore is not usable for cochlear implant patients without residual acoustic hearing. In addition, the pitch of electrodes is matched to the individual location-frequency map solely by manipulating the stimulation location, which in yet-to-be-implanted patients is the desired insertion depth of the electrode, or in already implanted electrodes is the electrode(s) to be activated.

U.S. Pat. No. 8,532,782 (Musical Fitting of Cochlear Implants; incorporated herein by reference in its entirety) describes a method for deriving electrode weighting factors for simultaneous electrode stimulation, i.e. for matching virtual-channel stimulation location to musical-interval rate-pitch percepts in a cochlear implant. But, the described method does not take into account individual rate-pitch saturation functions and uses a 1:1 mapping of the acoustic component frequencies to the electrical pulse rates.

U.S. Pat. No. 7,979,135 (Cochlear Implant Pitch Intensity; incorporated herein by reference in its entirety) describes a method for generating "electrode stimulation signals which have the intensity levels that reflect the pitch characteristics" of the acoustic stimulus frequency components, based upon "the relationship between stimulus intensity and pitch perception" in cochlear implants.

SUMMARY OF THE INVENTION

Embodiments of the present invention are directed to a signal processing arrangement and corresponding method that generates electrical stimulation signals to stimulation contacts in an implanted cochlear implant array. An input sound signal is decomposed into dominant psychophysically relevant frequency components, with each frequency component changing over time in frequency and level. Each frequency component is coded as a patient-specific, frequency-specific function of stimulation location, rate, and level to produce a sequence of requested stimulation events having an instantaneous frequency and level. And the electrical stimulation signals are generated from the requested stimulation events for delivery by the stimulation contacts to adjacent auditory neural tissue.

In further specific embodiments, decomposing the input sound signal may include using a psychophysical spectral masking model to select frequency components not masked by neighboring frequency components. And using the psychophysical spectral masking model may include establishing a maximum number of maximally spread frequency components based on one or both of spectral masking spread and/or temporal masking spread. Coding each frequency component may include assigning each frequency component a patient-specific stimulation rate based on stimulation location, and/or assigning a subclass of low frequency components to a stimulation rate equal to the instantaneous frequency of the requested stimulation events. The electrical stimulation signals may be configured for simultaneous stimulation of two or more stimulation contacts, or for sequential stimulation of the stimulation contacts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF SPECIFIC EMBODIMENTS

Embodiments of the present invention enable an optimal integration of all the different kinds of electrical stimulation cues needed for robust frequency perception: stimulation location, stimulation rate, and stimulation level. In general terms, the stimulation rates are primarily driven by relevant frequency components, especially for low frequencies.

Figure 9:
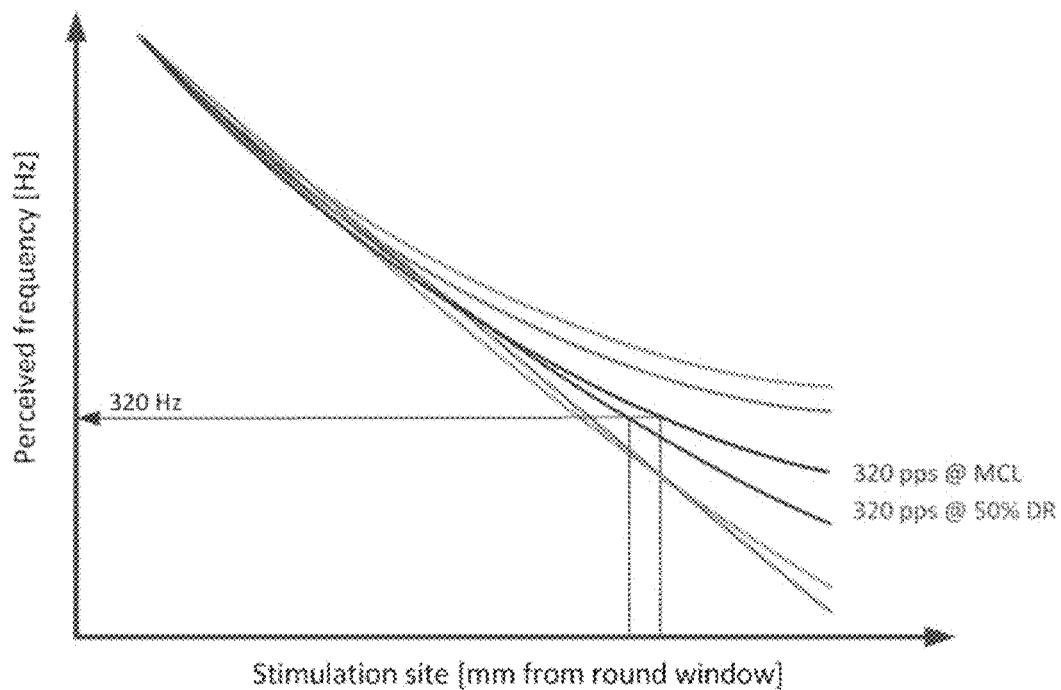
FIG. 9 shows an example of a frequency percept of 320 Hz elicited by a stimulation rate of 320 pps at a matched stimulation location.
Figure 10:
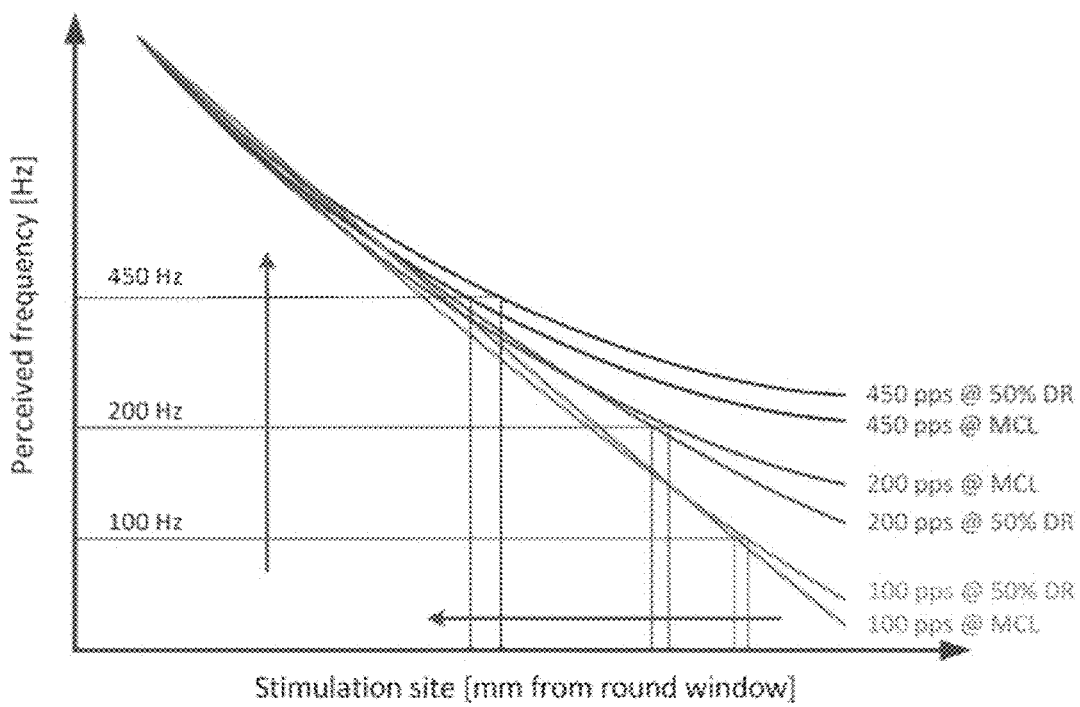
FIG. 10 shows different stimulation rates elicited according frequency percepts when stimulated at individually matched stimulation locations.

FIG. 9 shows an example of a frequency percept of 320 Hz elicited by a stimulation rate of 320 pps at a matched stimulation location. Furthermore, a change of an input frequency is translated into a change of stimulation rate and location. FIG. 10 shows how different stimulation rates elicit corresponding frequency percepts when stimulated at individually matched stimulation locations. Because the frequency percept for a fixed stimulation rate and location generally changes as a function of stimulation level, individually mapped functions of stimulation rate and location to perceived frequency will depend on the stimulation level. In addition, the translation from input frequency to stimulation location and rate varies according to the spectral level of the input frequency component (see FIG. 10).

Figure 11:
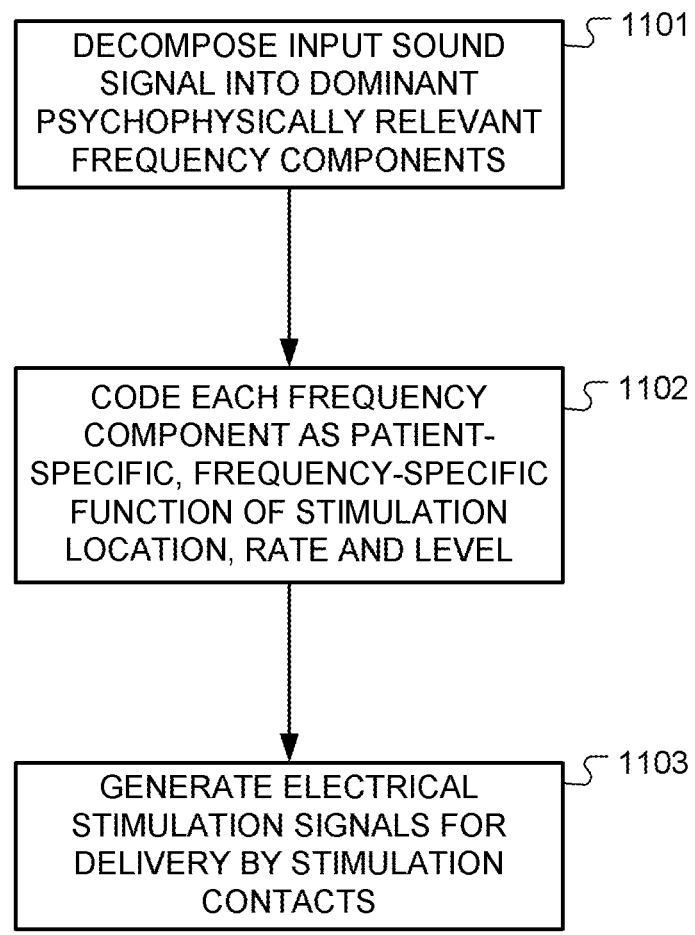
FIG. 11 is a flow chart showing various logical steps in producing electrical stimulation signals to stimulation contacts in an implanted cochlear implant array according to an embodiment of the present invention.

FIG. 11 is a flow chart showing various logical steps in producing electrical stimulation signals to stimulation contacts in an implanted cochlear implant array according to an embodiment of the present invention. A pseudo code example of such a method can be set forth as:

```
Input Frequency and Component Level Estimation:
    Decompose (input_sound, frequency_components)
Frequency to Rate-Place Matching:
    Code (frequency_components, req_stim_events)
Stimulation Pulse Generation:
    Generate (req_stim_events, output_pulses)
```

The details of such an arrangement are set forth in the following discussion.

Figure 1:
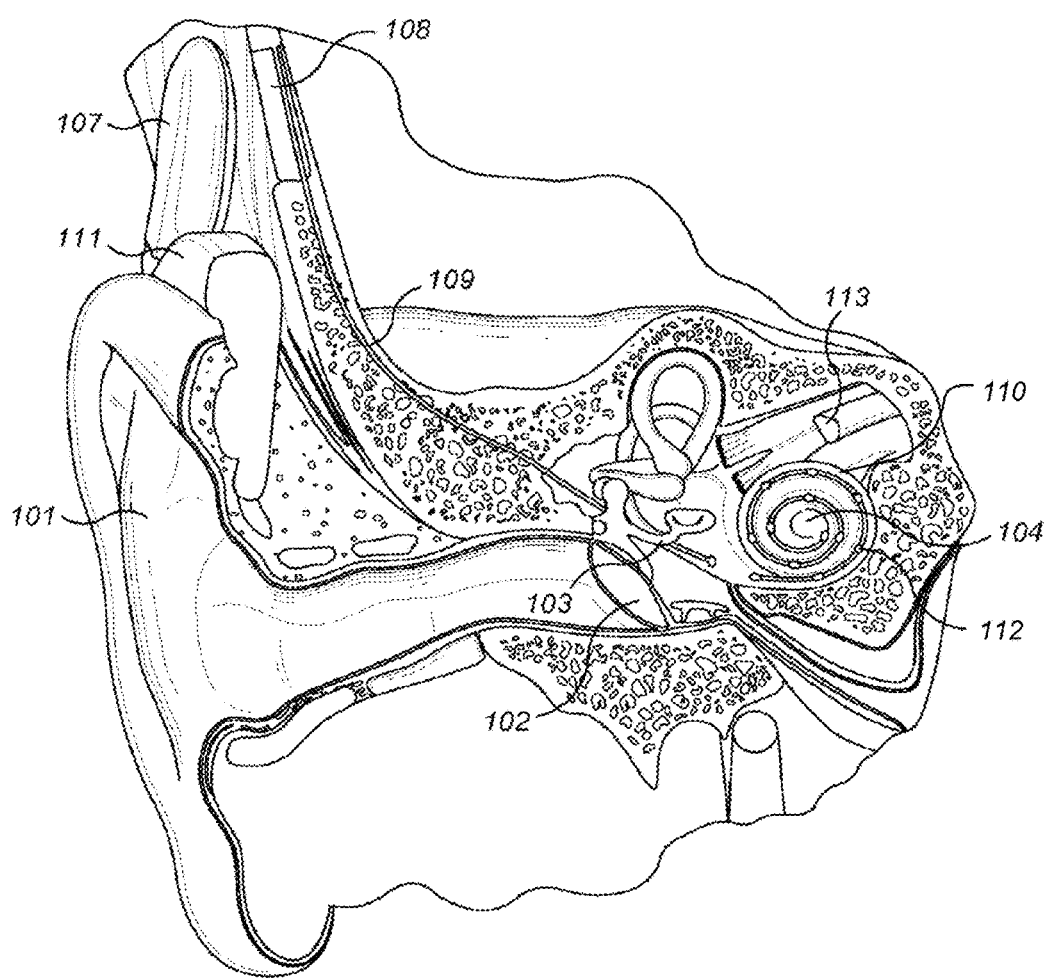
FIG. 1 shows a section view of a human ear with a typical cochlear implant system designed to deliver electrical stimulation to the inner ear.
Figure 2:
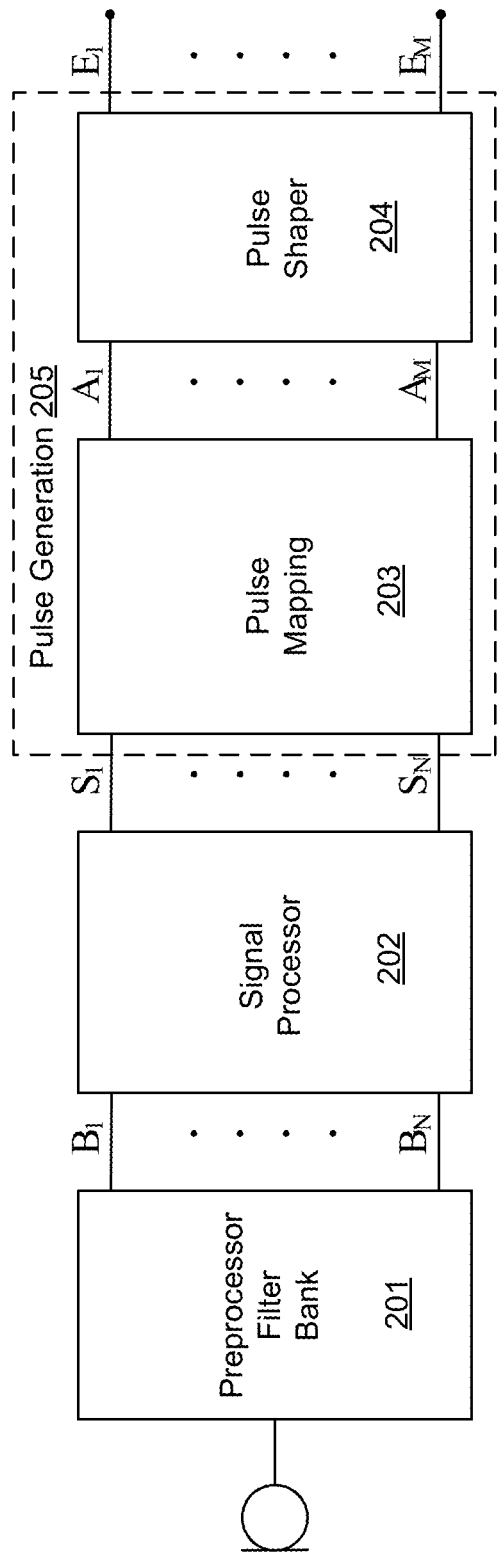
FIG. 2 shows various functional blocks in a continuous interleaved sampling (CIS) processing system.
Figure 3:
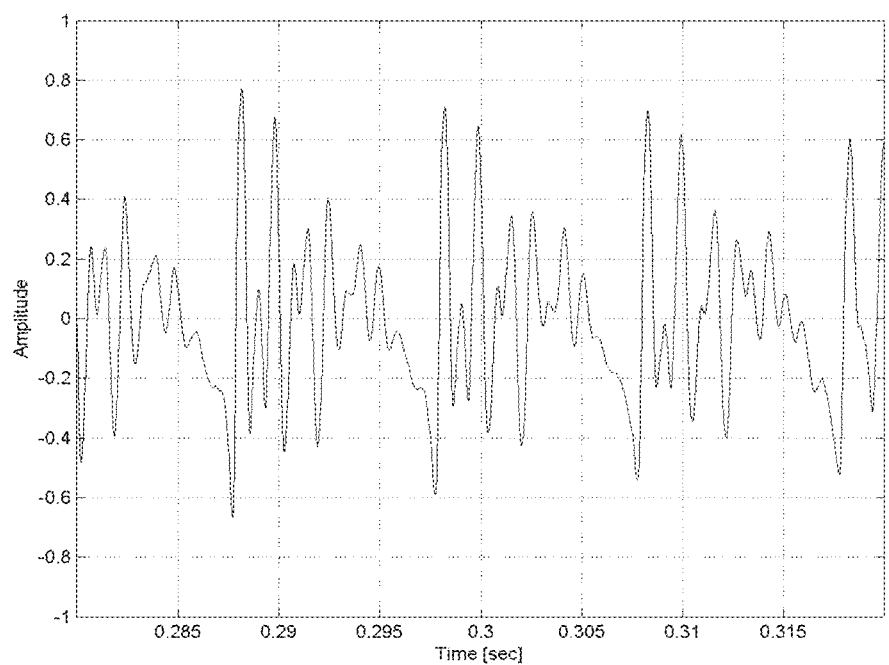
FIG. 3 shows an example of a short time period of an audio speech signal from a microphone.
Figure 4:
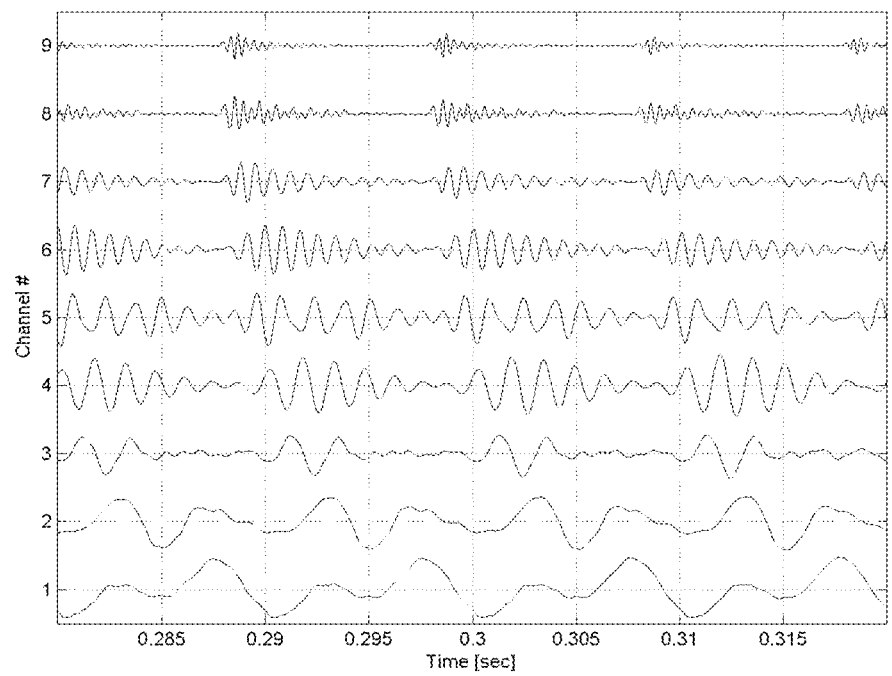
FIG. 4 shows an acoustic microphone signal decomposed by band-pass filtering by a bank of filters into a set of band pass signals.
Figure 5:
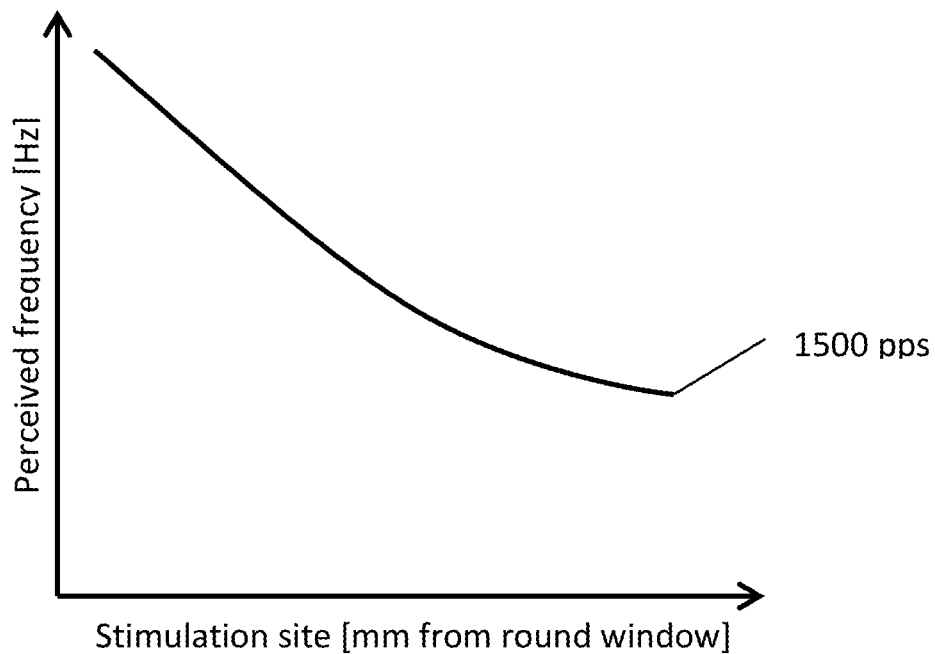
FIG. 5 shows an example of frequency percept elicited by electrical stimulation rate of 1500 pps at different intracochlear stimulation locations.
Figure 6:
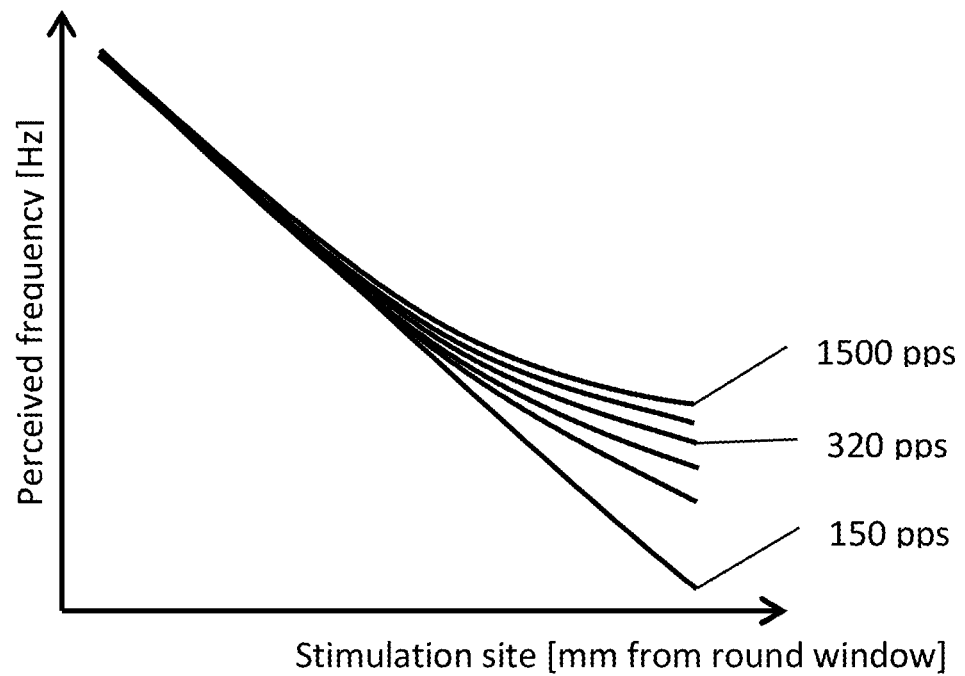
FIG. 6 shows examples of frequency percepts elicited at different intracochlear stimulation locations by different stimulation rates.
Figure 12:
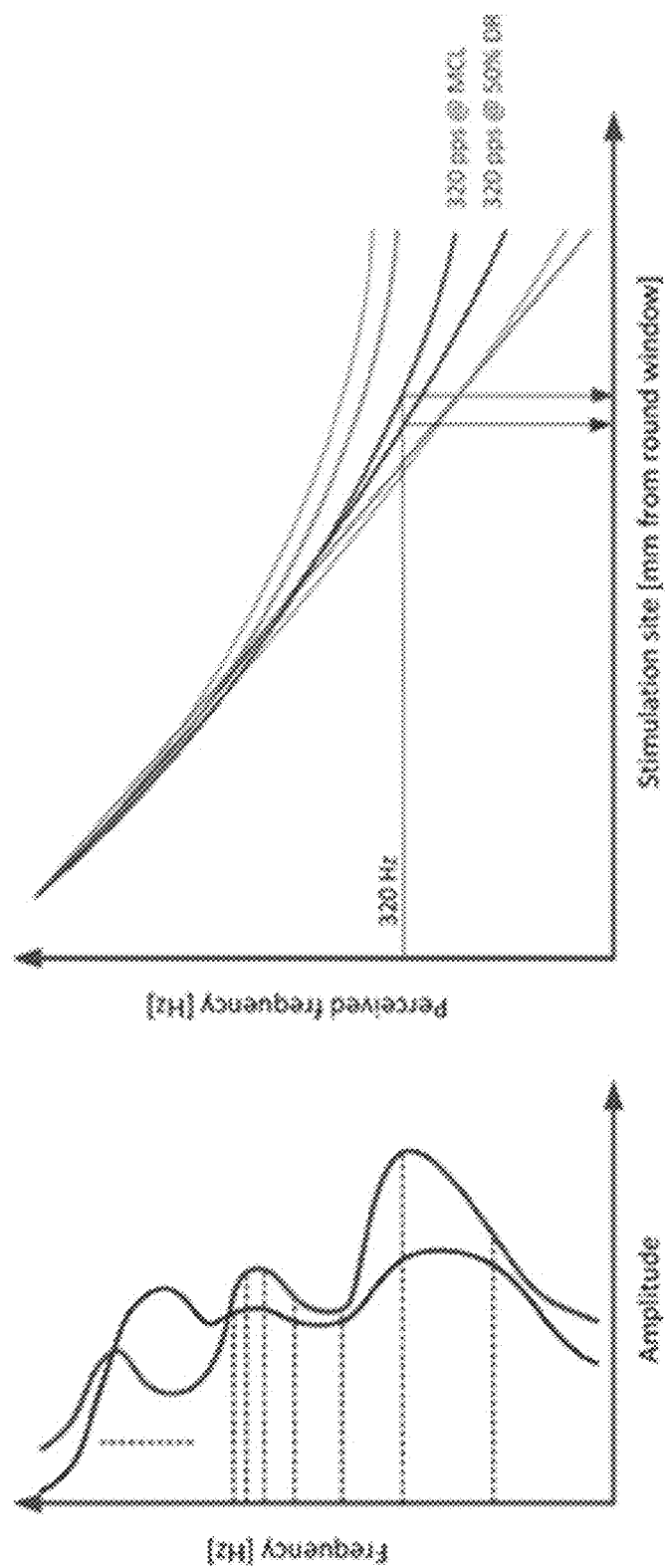
FIG. 12 shows a frequency component of an audio signal translated into a stimulation rate and stimulation location for best match of input frequency and frequency percept.

As in the arrangement discussed above with respect to FIG. 2, a preprocessor signal filter bank 201 can be configured to decompose an input sound signal into band pass signals $B_1$ to $B_M$, step 1101, representing an estimate of instantaneous input frequency and component level such that each band pass signal $B_1$ to $B_M$ corresponds to an associated dominant psychophysically relevant frequency component that changes over time in frequency and level. FIG. 12 shows how a frequency component of an input sound signal at a given spectral level can be translated into a stimulation rate and stimulation location for best match of input frequency and frequency percept. Note that the transfer function is level dependent.

Figure 13:
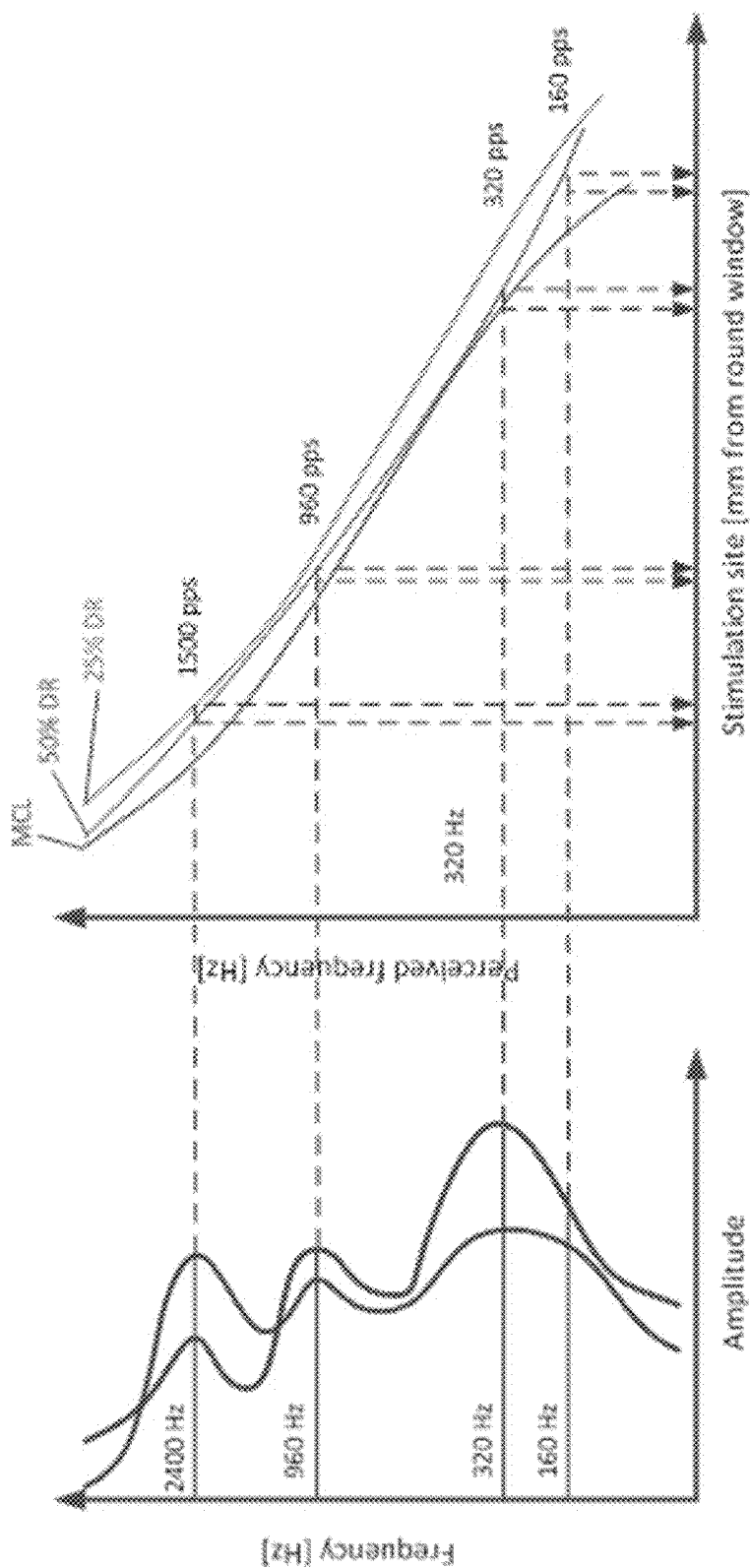
FIG. 13 shows translation of dominant and psychophysically relevant frequency components into individual stimulation rates and stimulation locations.

The preprocessor signal filter bank 201 can further apply a spectral masking model that represents dominant psychophysically relevant frequency components. Some maximum number of frequency components that are not masked by neighbouring frequency components are selected for further processing. The properties of the masking model such as spectral and/or temporal spread of masking can be defined in order to find a maximum number of maximally spread frequency components. FIG. 13 shows how the fundamental frequency (first harmonic) and formant frequencies (resonant higher harmonics) of a harmonic complex signal such as a voiced speech sound are selected based on the masking model.

Figure 14:
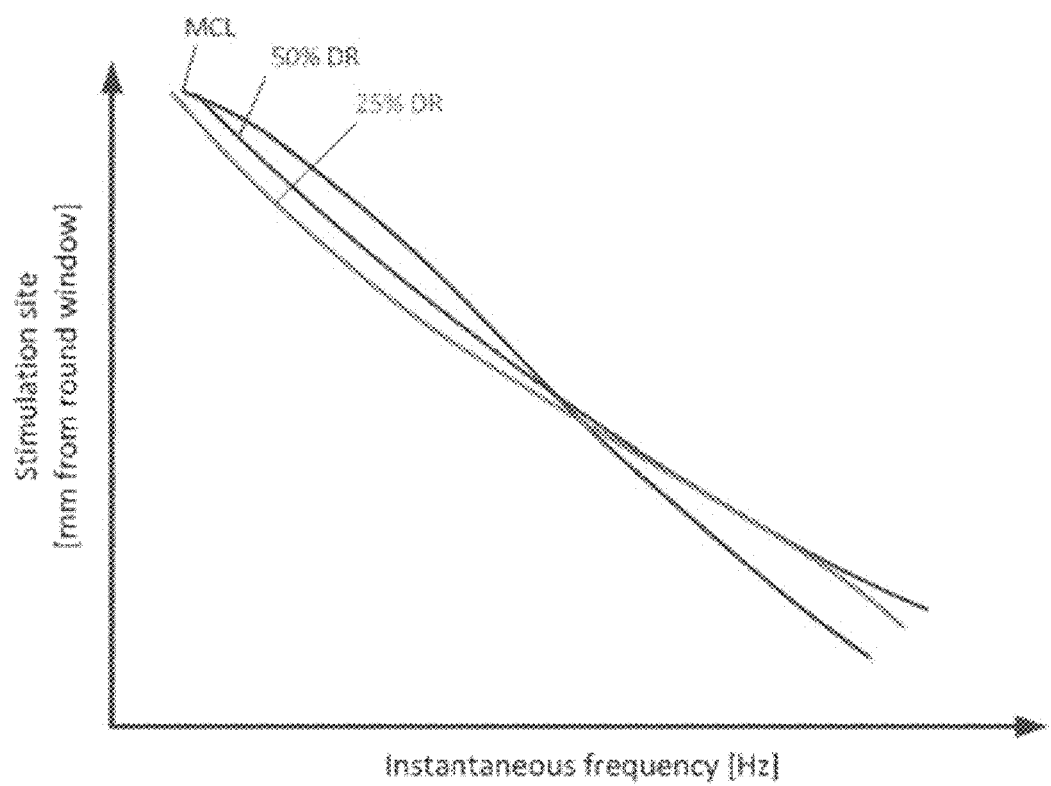
FIG. 14 shows stimulation location as a function of instantaneous frequency, for different frequency component levels mapped to corresponding stimulation levels within the electrical dynamic range.

The signal processing module 202 processes the frequency component band pass signals $B_1$ to $B_M$ to code each frequency component as a patient-specific, frequency-specific function of stimulation location, rate, and level, step 1202, to produce a sequence of requested stimulation events $S_1$ to $S_N$ that have an instantaneous frequency and level. This represents a matching of frequency to location-rate as a function of frequency component level. The signal processing module 202 assigns each frequency component to a user specific stimulation location depending on the selected stimulation location. FIG. 14 shows an example of stimulation location along the basilar membrane as a function of instantaneous frequency, for different frequency component levels mapped to corresponding stimulation levels within the electrical dynamic range.

Figure 15:
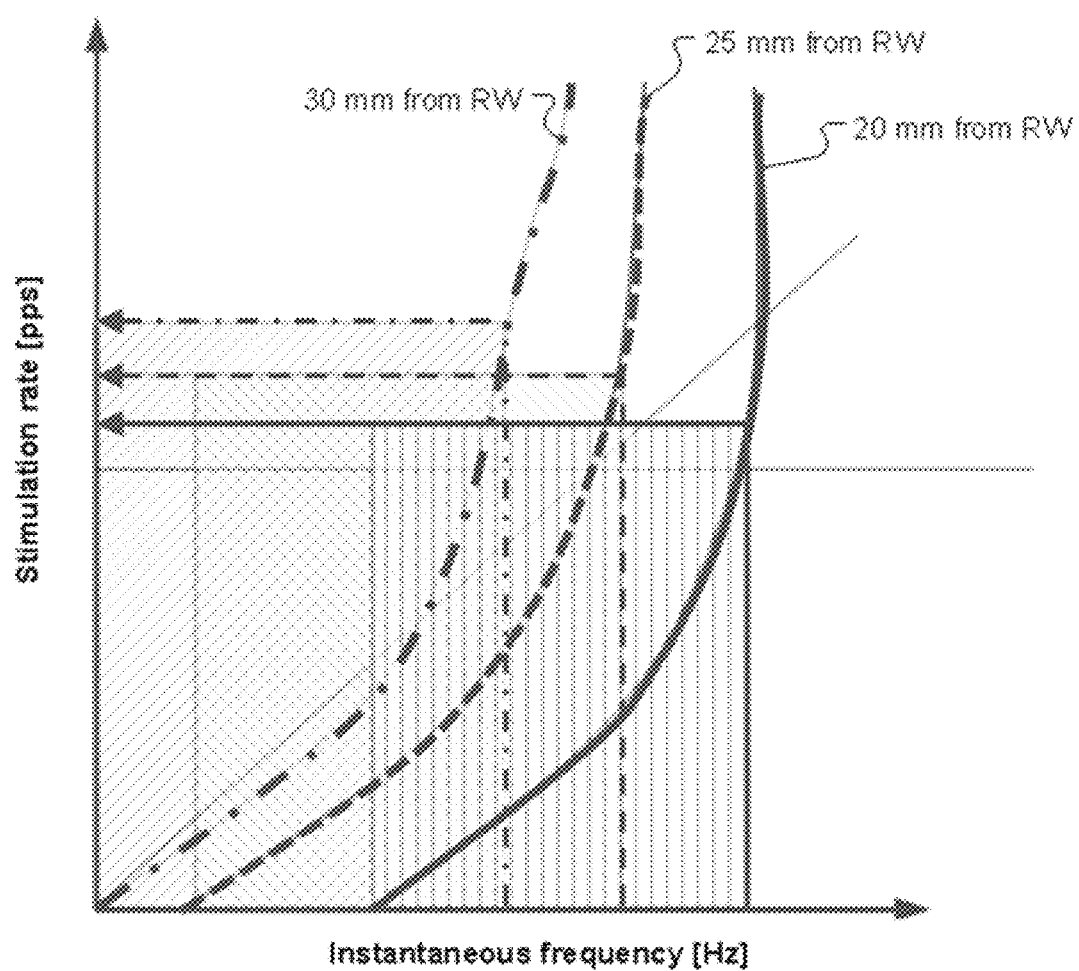
FIG. 15 shows stimulation rate as a function of instantaneous frequency, with location of stimulation level along the cochlea (distance from RW in mm) as parameter (three solid curves).

The signal processing module 202 also assigns each frequency component to a user specific stimulation rate depending on the selected stimulation location. FIG. 15 shows stimulation rate as a function of instantaneous frequency with stimulation location along the cochlea (distance from the round window in mm) as the parameter shown by the three solid curves. For lower frequencies, the stimulation rate can correspond to the instantaneous frequency, but at higher frequencies the stimulation rate can saturate. Because of rate-pitch saturation, the range of frequencies that can be mapped to stimulation rates (shaded rectangles in FIG. 15) is limited and depends on the stimulation location. Rate saturation limits can be derived from psychoacoustic/psychophysical measurements (e.g., rate-pitch saturation limit) or electro-physiologic measurements (e.g., a recovery function derived from electrically evoked potentials). In a given specific embodiment, rate-pitch mapping functions may be stored in multiple tables in processor memory which may be indexed according to the selected stimulation location and the frequency component level. The assignment of a frequency component to a patient-specific stimulation location and stimulation rate does depend on the component's spectral level. Functions for transferring component frequencies to patient-specific stimulation locations and rates can be determined at multiple stimulation levels within the patient's location-specific and rate-specific electrical dynamic range. For frequency component levels that result in intermediate stimulation levels within the mapped electrical dynamic range, location-rate transfer functions can be interpolated (see FIGS. 12, 14, and 15).

The pulse generator 205 is configured to convert the requested stimulation events $S_1$ to $S_N$ to produce a corresponding sequence of unweighted stimulation signals $A_1$ to $A_M$ that provide an optimal electric representation of the acoustic signal, and then apply a linear mapping function (typically logarithmic) and pulse shaping to produce weighted output pulse sequences electrical stimulation signals $E_1$ to $E_M$ for delivery by the stimulation contacts to adjacent auditory neural tissue, step 1203. The weighted output pulse sequences electrical stimulation signals $E_1$ to $E_M$ are adapted to the needs of the individual implant user based on a post-surgical fitting process that determines patient-specific perceptual characteristics.

Figure 16:
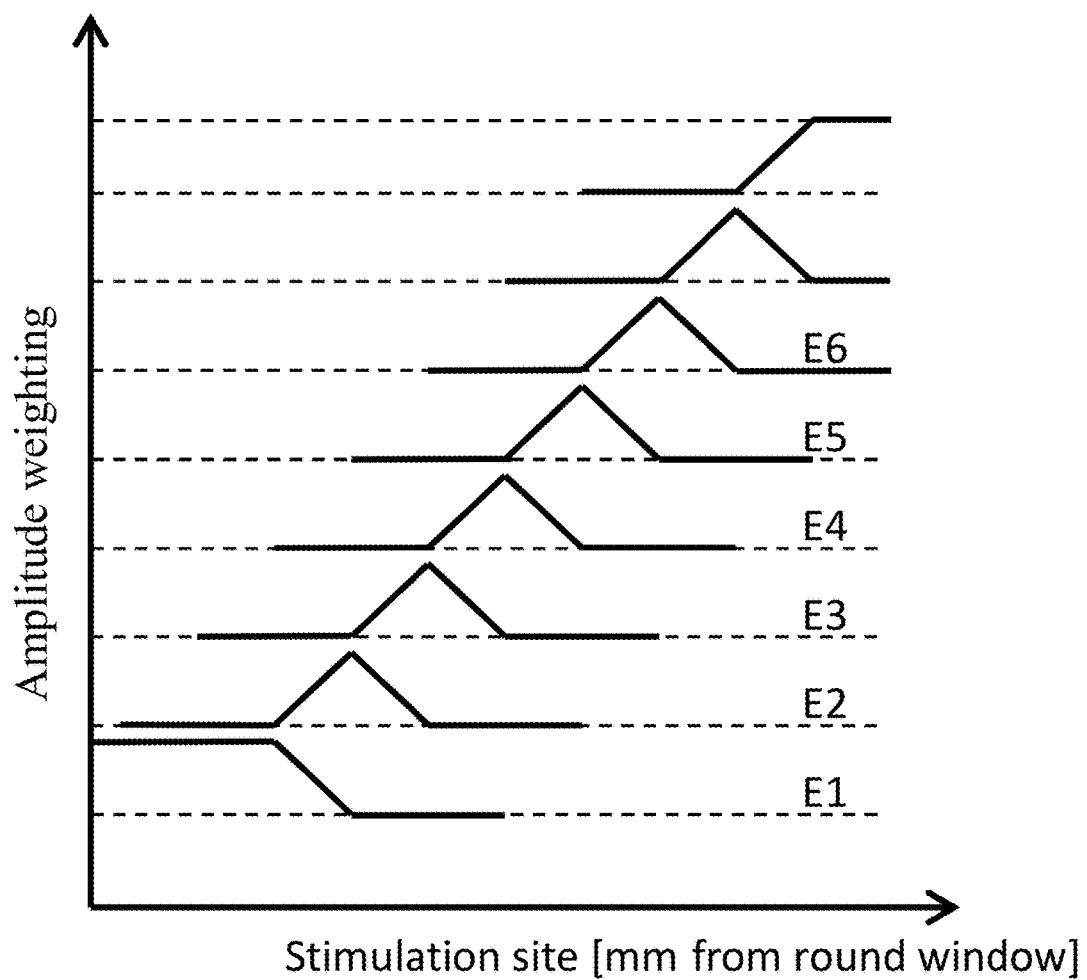
FIG. 16 shows electrode weighting (e.g. simultaneous stimulation of two adjacent electrodes) as a function of stimulation location.

The electrical stimulation signals $E_1$ to $E_M$ may be configured for simultaneous stimulation of two or more stimulation contacts, or for sequential stimulation of the stimulation contacts. Simultaneous stimulation requests are either translated into a simultaneous or fast sequential stimulation of a plurality of stimulation locations or into a stimulation of the event with the highest amplitude. (See FIG. 16). Electrical masking effects can be addressed by inhibition of stimulation in a defined region around and time after a stimulation pulse.

A given embodiment can be fitted to better resemble natural pitch by modifying the mapping function shown in FIG. 14. A user with an existing understanding of musical intervals can be asked to match certain intervals in different frequency ranges, e.g. a major third/fifth/octave, similar to tuning a piano. Based on that, the input frequency of the test tones is transformed into stimulation rates via the stimulation location-specific mapping function given in FIG. 15, while the stimulation location is controlled by modifying the mapping function given in FIG. 14 until the desired musical interval can be perceived. In a patient without an existing musical understanding, a frequency difference limen can be measured at different instantaneous frequencies. Then a small frequency interval (e.g. second) can be played at different neighboring locations within the cochlea by modifying the absolute value and/or slope of the mapping function given in FIG. 14. The slopes at which a second musical interval produces similarly high identification rates at different frequencies and places can be used to build a mapping function that produces perceptually equally distributed musical intervals. Alternatively, also the frequency-rate mapping function (FIG. 15) can be modified at a given frequency-location mapping function (FIG. 14).

In contrast to the approach described in U.S. Pat. No. 8,554,330, embodiments of the present invention use rate-location matching that:
 does not require any residual acoustic hearing and therefore is applicable to all cochlear implant recipients,
 achieves an electrode pitch match via level-dependent combined rate-location matching. Not only by manipulating/mapping the stimulation location as in U.S. Pat. No. 8,554,330, but also by manipulating/mapping the stimulation rate (both contribute to pitch perception in both normal and electrical hearing, especially at low stimulus frequencies),
 measures individual rate-location-frequency functions for patient mapping, either via musical pitch interval adjustments or frequency difference limen measurements, or via electro-physiologic measurements such as a recovery functions derived from electrically evoked potentials.

In contrast to the arrangement described in U.S. Pat. No. 8,532,782, embodiments of the present invention use rate-location matching that does not rely on a 1:1 relationship between acoustic stimulus component frequency and electrical stimulation rate, but which takes into account individual rate-pitch saturation functions for mapping component frequencies to individual rates of stimulation (FIG. 15).

Figure 7:
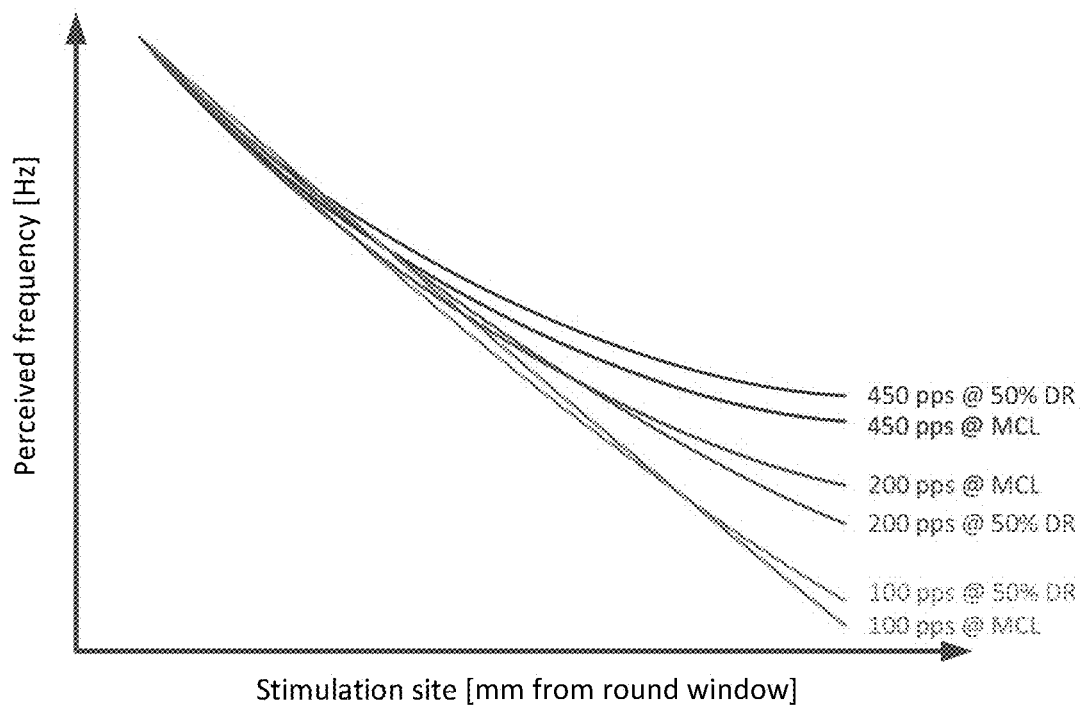
FIG. 7 shows frequency percepts elicited at different intracochlear stimulation locations by different stimulation rates presented at different stimulation levels.
Figure 8:
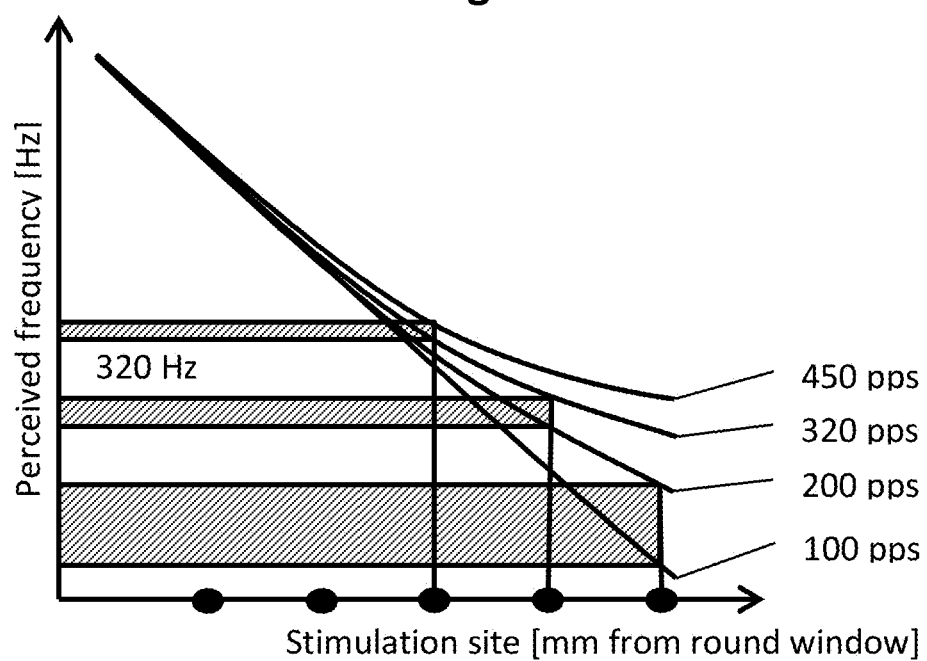
FIG. 8 sows non-overlapping frequency ranges perceived by stimulating three adjacent electrodes at band specific stimulation rates.

Prior art arrangements such as in U.S. Pat. No. 8,554,330; U.S. Pat. No. 8,532,782; and U.S. Pat. No. 7,979,135 describe mapping acoustic stimulus component frequency to electrical pitch by exploiting just a single dimension of electrical pitch perception in isolation (stimulation location, rate, and level, respectively). Embodiments of the present invention take into account the reality that electrical pitch depends on a complex interaction of all three stimulus dimensions of location, rate, and level, and that this interaction varies across individual cochlear implant recipients. Nor are embodiments of the present invention simply a combination the three patents above, because they do not rely on general functions such as the Greenwood location-frequency function or a 1:1 correspondence between component frequency and stimulation rate, but rather they take into account individual location-frequency and rate-pitch functions (FIG. 7) and they use methods to determine those individual mapping functions. In addition, embodiments of the present invention inherently reflect the complex interactions between the three pitch stimulus dimensions to achieve the best possible match. For example, pitch is generally dominated by stimulation rate at low component frequencies, and by stimulation location at higher component frequencies (FIG. 12) and can change as a function of stimulation level (FIG. 13).

Embodiments of the invention may be implemented in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for generating electrical stimulation signals to stimulation contacts in an implanted cochlear implant electrode array, the method comprising:
    decomposing an input sound signal into a plurality of dominant psychophysically relevant frequency components, with each frequency component changing over time in frequency and level;
    coding each frequency component as a patient-specific, frequency-specific function of stimulation location, rate, and level to produce a sequence of requested stimulation events having an instantaneous frequency and level with an electrode pitch match via level-dependent combined rate-location matching; and
    generating the electrical stimulation signals from the requested stimulation events for delivery by the stimulation contacts to adjacent auditory neural tissue.

2. The method according to claim 1, wherein decomposing the input sound signal includes using a psychophysical spectral masking model to select frequency components not masked by neighboring frequency components.

3. The method according to claim 2, wherein using the psychophysical spectral masking model includes establishing a maximum number of maximally spread frequency components based on one or both of spectral masking spread and/or temporal masking spread.

4. The method according to claim 1, wherein coding each frequency component includes assigning each frequency component a patient-specific stimulation rate based on stimulation location.

5. The method according to claim 1, wherein coding each frequency component includes assigning a subclass of low frequency components to a stimulation rate equal to the instantaneous frequency of the requested stimulation events.

6. The method according to claim 1, wherein the electrical stimulation signals are configured for simultaneous stimulation of two or more stimulation contacts.

7. The method according to claim 1, wherein the electrical stimulation signals are configured for sequential stimulation of the stimulation contacts.

8. A system for generating electrical stimulation signals to stimulation contacts in an implanted cochlear implant electrode array, the arrangement comprising:
    a signal filter bank configured to decompose an input sound signal into a plurality of dominant psychophysically relevant frequency components, with each frequency component changing over time in frequency and level;
    a signal processing module configured to code each frequency component as a patient-specific, frequency-specific function of stimulation location, rate, and level to produce a sequence of requested stimulation events having an instantaneous frequency and level with an electrode pitch match via level-dependent combined rate-location matching; and
    a pulse generator configured to generate the electrical stimulation signals from the requested stimulation events for delivery by the stimulation contacts to adjacent auditory neural tissue.

9. The system according to claim 8, wherein the signal filter bank is configured to decompose the input sound signal based on using a psychophysical spectral masking model to select frequency components not masked by neighboring frequency components.

10. The system according to claim 9, wherein the signal filter bank is configured to use the psychophysical spectral masking model by establishing a maximum number of maximally spread frequency components based on one or both of spectral masking spread and/or temporal masking spread.

11. The system according to claim 8, wherein the signal processing module is configured to code each frequency component based on assigning each frequency component a patient-specific stimulation rate based on stimulation location.

12. The system according to claim 8, wherein the signal processing module is configured to code each frequency component based on assigning a subclass of low frequency components to a stimulation rate equal to the instantaneous frequency of the requested stimulation events.

13. The system according to claim 8, wherein the pulse generator is configured to generate simultaneous electrical stimulation signals for two or more stimulation contacts.

14. The system according to claim 8, wherein the pulse generator is configured to generate sequential electrical stimulation signals for the stimulation contacts.

15. A non-transitory tangible computer-readable medium having instructions thereon for generating electrical stimulation signals to stimulation contacts in an implanted cochlear implant electrode array, the instructions comprising:
    decomposing an input sound signal into a plurality of dominant psychophysically relevant frequency components, with each frequency component changing over time in frequency and level;
    coding each frequency component as a patient-specific, frequency-specific function of stimulation location, rate, and level to produce a sequence of requested stimulation events having an instantaneous frequency and level with an electrode pitch match via level-dependent combined rate-location matching; and
    generating the electrical stimulation signals from the requested stimulation events for delivery by the stimulation contacts to adjacent auditory neural tissue.

16. The computer-readable medium according to claim 15, wherein the instructions for decomposing the input sound signal include instructions for using a psychophysical spectral masking model to select frequency components not masked by neighboring frequency components.

17. The computer-readable medium according to claim 16, wherein the instructions for using the psychophysical spectral masking model include instructions for establishing a maximum number of maximally spread frequency components based on one or both of spectral masking spread and/or temporal masking spread.

18. The computer-readable medium according to claim 15, wherein the instructions for coding each frequency component include instructions for assigning each frequency component a patient-specific stimulation rate based on stimulation location.

19. The computer-readable medium according to claim 15, wherein the instructions for coding each frequency component include instructions for assigning a subclass of low frequency components to a stimulation rate equal to the instantaneous frequency of the requested stimulation events.

20. The computer-readable medium according to claim 15, wherein the electrical stimulation signals are configured for simultaneous stimulation of two or more stimulation contacts.

21. The computer-readable medium according to claim 15, wherein the electrical stimulation signals are configured for sequential stimulation of the stimulation contacts.

* * * * *